(12) United States Patent
Mizumoto

(10) Patent No.: US 11,890,176 B2
(45) Date of Patent: Feb. 6, 2024

(54) ABSORBENT ARTICLE

(71) Applicant: DAIO PAPER CORPORATION, Ehime (JP)

(72) Inventor: Yousei Mizumoto, Tochigi (JP)

(73) Assignee: DAIO PAPER CORPORATION, Ehime (JP)

(*) Notice: Subject to any disclaimer, the term of this patent is extended or adjusted under 35 U.S.C. 154(b) by 875 days.

(21) Appl. No.: 16/962,318

(22) PCT Filed: Mar. 11, 2019

(86) PCT No.: PCT/JP2019/009807
§ 371 (c)(1),
(2) Date: Jul. 15, 2020

(87) PCT Pub. No.: WO2019/188223
PCT Pub. Date: Oct. 3, 2019

(65) Prior Publication Data
US 2020/0337911 A1    Oct. 29, 2020

(30) Foreign Application Priority Data
Mar. 26, 2018    (JP) .................. 2018-057861

(51) Int. Cl.
*A61F 13/494*    (2006.01)
*A61F 13/532*    (2006.01)
*A61F 13/53*    (2006.01)

(52) U.S. Cl.
CPC .......... *A61F 13/494* (2013.01); *A61F 13/532* (2013.01); *A61F 2013/530941* (2013.01)

(58) Field of Classification Search
CPC .................. A61F 13/494; A61F 13/532; A61F 2013/4953; A61F 2013/530941;
(Continued)

(56) References Cited

U.S. PATENT DOCUMENTS

| 4,820,295 A | 4/1989 | Chapas et al. |
| 4,834,735 A | 5/1989 | Alemany et al. |

(Continued)

FOREIGN PATENT DOCUMENTS

| GB | 2082643 | 3/1982 |
| JP | S63-109859 | 5/1988 |

(Continued)

OTHER PUBLICATIONS

Extended European Search Report for 19777756.8 dated Apr. 20, 2021.

(Continued)

*Primary Examiner* — Leslie Lopez
*Assistant Examiner* — Timothy L Flynn
(74) *Attorney, Agent, or Firm* — IPUSA, PLLC

(57) ABSTRACT

An absorbent article includes a liquid-permeable topsheet, a liquid-impermeable backsheet, and an absorbent body provided between the topsheet and the backsheet, wherein the absorbent body includes a crotch-corresponding region corresponding to the wearer's crotch when worn, and a front region being adjacent to and forward of the crotch-corresponding region, and a rear region being adjacent to and rearward of the crotch-corresponding region, and has a variable-density portion with a density increasing stepwise or gradually from a front toward a rear, the variable-density portion being located in a region extending at least from the crotch-corresponding region to the rear region.

8 Claims, 14 Drawing Sheets

(58) Field of Classification Search
CPC .... A61F 2013/1543; A61F 2013/15439; A61F 2013/530927; A61F 2013/530934; A61F 2013/15528; A61F 2013/15536; A61F 13/4704; A61F 13/49001; A61F 13/533; A61F 2013/15422
See application file for complete search history.

(56) References Cited

U.S. PATENT DOCUMENTS

| | | | | |
|---|---|---|---|---|
| 5,149,334 | A | * | 9/1992 | Lahrman ........... A61F 13/53717 604/367 |
| 5,348,547 | A | | 9/1994 | Payne et al. |
| 5,484,429 | A | | 1/1996 | Vukos et al. |
| 6,441,268 | B1 | | 8/2002 | Edwardsson |
| 6,563,013 | B1 | * | 5/2003 | Murota ................ A61F 13/533 604/385.01 |
| 2012/0316526 | A1 | * | 12/2012 | Rosati ................... A61K 45/06 604/366 |
| 2017/0246056 | A1 | | 8/2017 | Tagomori et al. |

FOREIGN PATENT DOCUMENTS

| | | |
|---|---|---|
| JP | H02-030326 U | 2/1990 |
| JP | H08-508662 | 9/1996 |
| JP | 2009-131417 | 6/2009 |
| JP | 5836782 | 12/2015 |
| JP | 2016-049199 | 4/2016 |

OTHER PUBLICATIONS

International Search Report for PCT/JP2019/009807 dated Jun. 4, 2019.

* cited by examiner

FIG.8
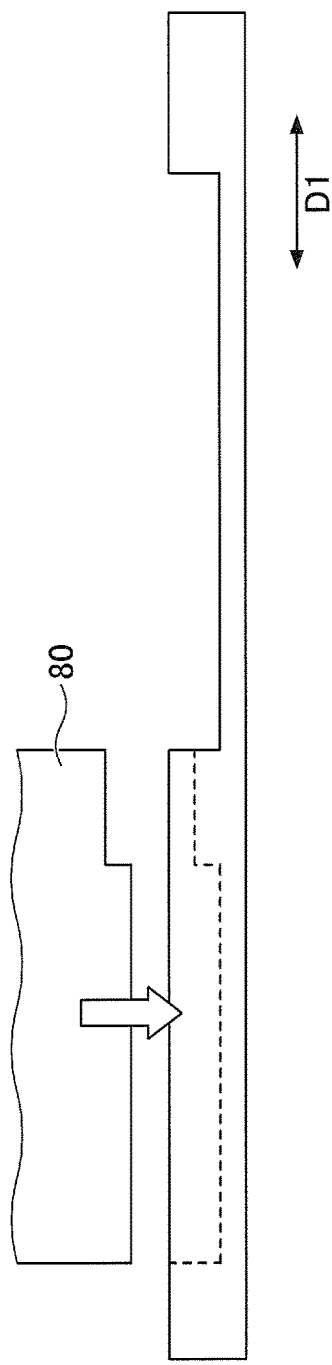
(a)
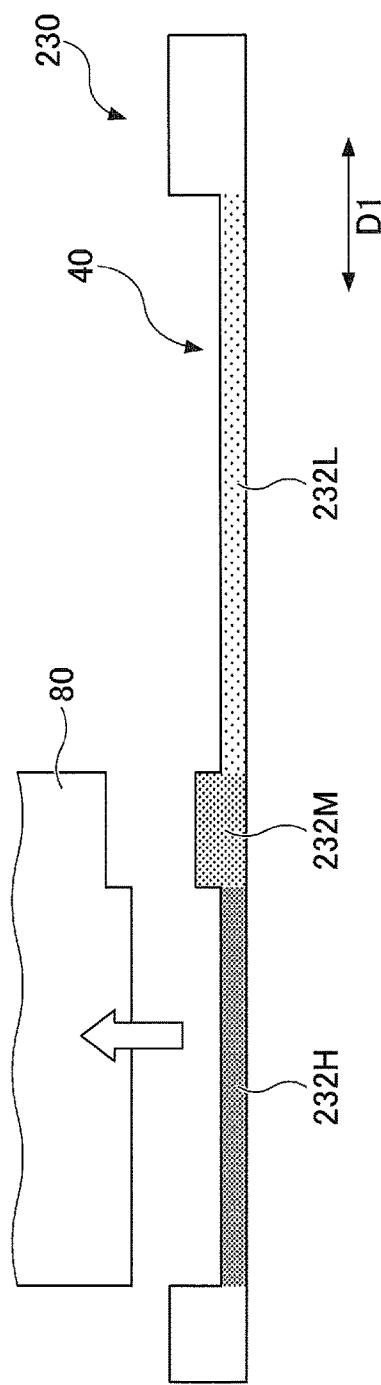
(b)

ABSORBENT ARTICLE

TECHNICAL FIELD

The present invention relates to an absorbent article.

BACKGROUND ART

Disposable diapers such as pad-type, tape-type, and underpants-type diapers, as well as sanitary napkins are known as absorbent articles. Such absorbent articles are typically configured to include a liquid-permeable topsheet, a liquid-impermeable backsheet, and an absorbent body provided between the topsheet and the backsheet.

In the absorbent article, in order to utilize not only the area in which a biofluid is discharged and its surroundings, but the whole absorbent body, the absorbent body preferably has an improved biofluid diffusibility, and therefore a variety of configurations have been proposed. As an example, a conventional configuration is known that includes an absorbent body in which a groove extending in the front-rear direction is provided, to facilitate a transfer of biofluid in the front-rear direction (see Patent Literature 1, for example).

CITATION LIST

Patent Literature

Patent Literature 1: Japanese Patent No. 5836782

SUMMARY OF INVENTION

Technical Problem

However, with the configuration only having a groove as described in Patent Literature 1, the biofluid may be transferred rearward very rapidly when a large amount of biofluid is discharged all at once. In that case, the amount of the absorbed biofluid may be uneven between the front and the rear of the absorbent body, which may even hinder the utilization of the entire absorbent body.

In view of above, an object of embodiments of the present invention is to provide an absorbent article in which a biofluid can be transferred at an appropriate rate, so as to utilize a greater extent of the absorbent body in the front-rear direction.

Solution to Problem

A first embodiment of the present invention provides an absorbent article including a liquid-permeable topsheet, a liquid-impermeable backsheet, and an absorbent body provided between the topsheet and the backsheet, wherein the absorbent body includes a crotch-corresponding region corresponding to the wearer's crotch when worn, and a front region being adjacent to and forward of the crotch-corresponding region, and a rear region being adjacent to and rearward of the crotch-corresponding region, and has a variable-density portion in which the density increases stepwise or gradually from a front toward a rear, the variable-density portion being provided in a region extending at least from the crotch-corresponding region to the rear region.

Advantageous Effects of Invention

According to an embodiment of the present invention, an absorbent article is provided in which biofluid can be transferred at an appropriate rate, so as to utilize a greater extent of the absorbent body in the front-rear direction.

BRIEF DESCRIPTION OF DRAWINGS

FIG. 8 is a view illustrating a manufacture of the absorbent body shown in FIG. 7.

DESCRIPTION OF EMBODIMENTS

Embodiments of the present invention will now be described with reference to the drawings. In each drawing, unless otherwise noted, the same or corresponding elements may be indicated with same reference number, and the description therefore may not be repeated.

Figure 1:
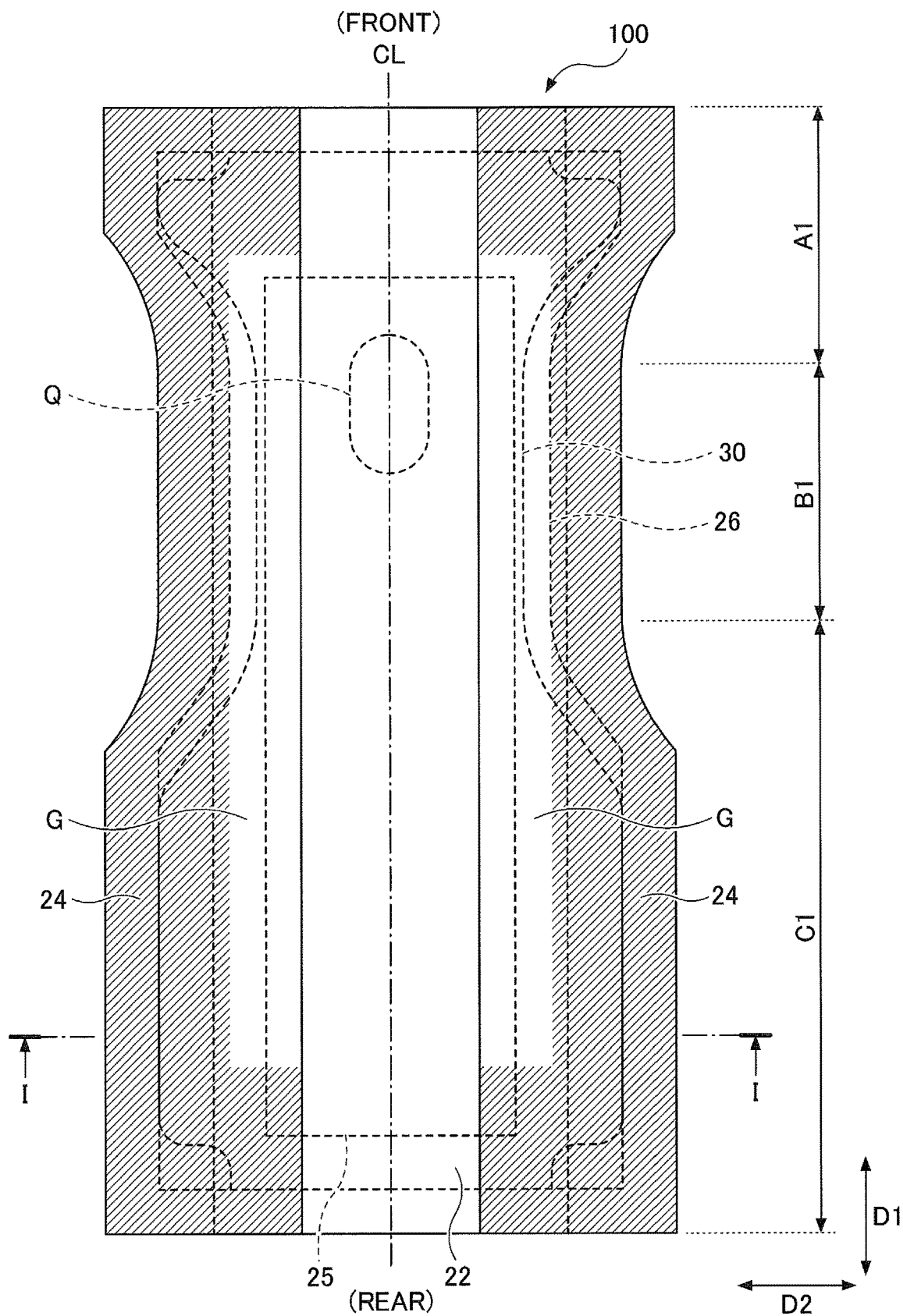
FIG. 1 is a planar view of an absorbent article according to an embodiment of the present invention.
Figure 2:
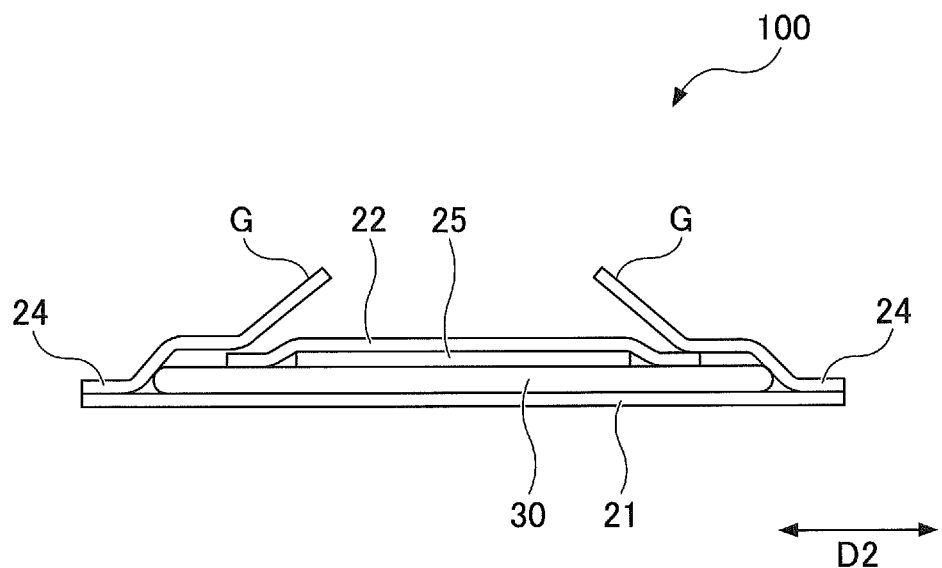
FIG. 2 is a cross-sectional view taken along the line I-I in FIG. 1.

FIG. 1 shows an overhead view of an absorbent article 100 according to an embodiment of the present invention. FIG. 2 shows a cross-sectional view taken along the line I-I in FIG. 1. In this embodiment, a pad-type disposable diaper (urine collection pad) is illustrated as an example.

As shown in FIGS. 1 and 2, the absorbent article 100 includes a liquid-permeable topsheet 22, a liquid-impermeable backsheet 21, and an absorbent 30 provided between the sheets 21 and 22. As shown in FIG. 1, the absorbent body 30 may be wrapped with a wrapping sheet 26 made of a nonwoven fabric, crepe paper, or the like. The wrapping sheet 26 may be uncolored (or white) or colored. When the absorbent article 100 is worn, the topsheet 22 side is the skin side, and the backsheet 21 side is secured to an outer diaper (an outside diaper), an underwear, or the like.

In this embodiment, the absorbent article 100 has an elongated shape as a whole in a planar view. That is, the absorbent article 100 has a predetermined length in a first direction (the front-rear direction or the longitudinal direction) D1 and a predetermined width in a second direction (the width direction) D2 perpendicular to the first direction D1, and the predetermined width is smaller than the predetermined length. The front and the rear of the absorbent article 100 respectively correspond to the ventral side and the dorsal side when the absorbent article is worn. The shape of the absorbent article 100 may be line-symmetric with respect to a front-rear direction centerline CL as shown in the drawings, or may be non-line-symmetric. The configuration of the absorbent article 100 (including the thickness, the basis weight of the absorbent body, the groove, etc.) may also be line-symmetric or non-line-symmetric.

As shown in FIG. 1, the absorbent article 100 has a crotch-corresponding region B1 substantially in the middle in the front-rear direction D1. In this specification, the "crotch-corresponding region" means a portion corresponding to the body's crotch (groin) during use of the absorbent article. For example, the crotch-corresponding region B1 may extend from the middle in the front-rear direction of the absorbent article or its proximity to a predetermined position in the front, or may extend over a predetermined extent in the middle in the front-rear direction of the absorbent article. In the illustrated embodiment, the absorbent article 100 includes a constricted portion having a smaller width, and a part of a region in which the constricted portion is formed corresponds to the crotch-corresponding portion. Further, a region adjacent to the front of the crotch-corresponding region B1 and extending to the front edge of the absorbent article 100, is the front region A1. A region adjacent to the rear edge of the crotch-corresponding region B1 and extending to the rear edge of the absorbent article 100 is the rear region C1.

As described above, the absorbent article 100 is not limited to a planar shape with a portion having a smaller width than the front and rear regions (i.e., a constricted portion), but may have another shape, such as a rectangular shape that has a constant width in the front-rear direction D1.

The entire length (the length in the front-rear direction D1) of the absorbent article 100 may be approximately 350 to 700 mm, and the entire width (the length in the width direction D2) may be approximately 130 to 400 mm. Further, the length of the crotch-corresponding region B1 in the front-rear direction D1 may be approximately 10 to 150 mm, the length of the rear region A1 in the front-rear direction D1 may be approximately 50 to 350 mm, and the length of the rear region C1 in the front-rear direction D1 may be approximately 50 to 350 mm. When the absorbent article 100 has a constricted portion, the minimum width of the absorbent article 100 is approximately 50 to 90% with respect to the entire width (the length in the width direction D2 in the portion forward of or rearward of the constricted portion).

As shown in FIG. 1, the size of the backsheet 21 may be larger than the absorbent body 30. The absorbent body 30 may be arranged within the area of the backsheet 21. The liquid-impermeable backsheet 21 may include a polyethylene film or the like, or may be a sheet having a moisture-permeability without impairing a water shielding property to prevent stuffiness. An example of such water shielding/moisture-permeable sheet includes a microporous sheet. The microporous sheet may be obtained by melt-kneading an olefin resin such as polyethylene or polypropylene with an inorganic filler to form a sheet, and subsequently stretching the sheet in a uniaxial direction or biaxial directions. The outer surface of the backsheet 21 may be covered with an outer sheet, such as a nonwoven fabric.

The topsheet 22 is disposed on the topside of the absorbent body 30. In the illustrated embodiment, the topsheet 22 does not cover a part of the ends of the width direction D2 of the absorbent 30 body, but the topsheet 22 may cover the entire absorbent body 30. The topsheet 22 may include a porous or nonporous nonwoven fabric, a perforated plastic sheet, and the like. Examples of material fibers forming the nonwoven fabric may include synthetic fibers such as olefin-based fibers including polyethylene and polypropylene, polyester-based fibers, amide-based fibers, and the like, as well as regenerated fibers such as rayon and cupra, and natural fibers such as cotton.

As shown in FIGS. 1 and 2, an intermediate sheet 25 can be interposed between the topsheet 22 and the absorbent body 30. The intermediate sheet 25 prevents reversal of the biofluid once absorbed in the absorbent body 30. Therefore, the intermediate sheet 25 may preferably be made of a material having a low water-retention property and a high liquid-permeability, such as a variety of nonwoven fabrics, a mesh film, or the like.

At both ends of the front-rear direction D1 of the absorbent body 30, the backsheet 21 and the topsheet 22 are bonded with each other. Further, gather sheets 24, 24 are each provided on lateral ends of the absorbent article 100 along the front-rear direction D1, and the backsheet 21 and the gather sheets 24, 24 are bonded with each other on each lateral side of the width direction D2 of the absorbent article 100.

Suitable material for the gather sheet 24 may include a plastic sheet, a melt-blown nonwoven fabric, or the like may be used. However, in order to provide a comfortable touch to the skin, the nonwoven fabric treated with water-repellent material such as silicone may preferably be used.

As shown in FIGS. 1 and 2, the gather sheets 24, 24 are each superimposed on the topsheet 22. The inner end of the width direction D2 of each gather sheet 24 may be provided with an elastic member that is attached in its stretched state along the front-rear direction D1 to the sheet. The elastic member may be manufactured from a styrene-based rubber, an olefin-based rubber, a urethane-based rubber, an ester-based rubber, or the like, to form a thread, a string, a band, etc.

The gather sheet 24 may also be bonded to the topsheet 21, the wrapping sheet 26, or the backsheet 21 disposed directly under the gather sheet 24 in the zone shown by a linear hatching in FIG. 1. Because the inner end of the width direction D2 of the gather sheet 24 may be provided with an elastic member as described above, the unbonded portion in each gather sheet 24 (i.e., the inner region in the width direction D2 excluding the front and rear edges of the gather sheet 24) can stand from the topside (the topsheet side) of the absorbent article 100 to form each of gathers G, G. The gathers G, G enable the prevention of lateral leakage of biofluids.

The bonding between the gather sheets 24, 24 and the components thereunder can be formed, for example, by a hot-melt adhesive, a heat sealing, or an ultrasonic sealing.

The absorbent body 30 may be a stacked fibrous body of pulp fibers, an assembly of filaments such as cellulose acetate, a nonwoven fabric, or the like. A superabsorbent polymer in particulate form may be mixed to or fixed to the absorbent body, as necessary. When the superabsorbent polymer particles are mixed, the absorbent body 30 may preferably be wrapped in a wrapping sheet 26 to prevent spillage of the particulates.

The basis weight of the fiber and the basis weight of the superabsorbent polymer in the absorbent body 30 may be appropriately determined. However, the basis weight of the fiber may preferably be approximately 100 to 700 $g/m^2$, and the basis weight of the absorbent polymer may preferably be approximately 50 to 550 $g/m^2$. The thickness of the absorbent body 30 (the thickness of a part excluding a grooved part, which is an average value if the thickness is not uniform) may be approximately 1 to 30 mm, or may be approximately 5 to 25 mm.

Figure 3:
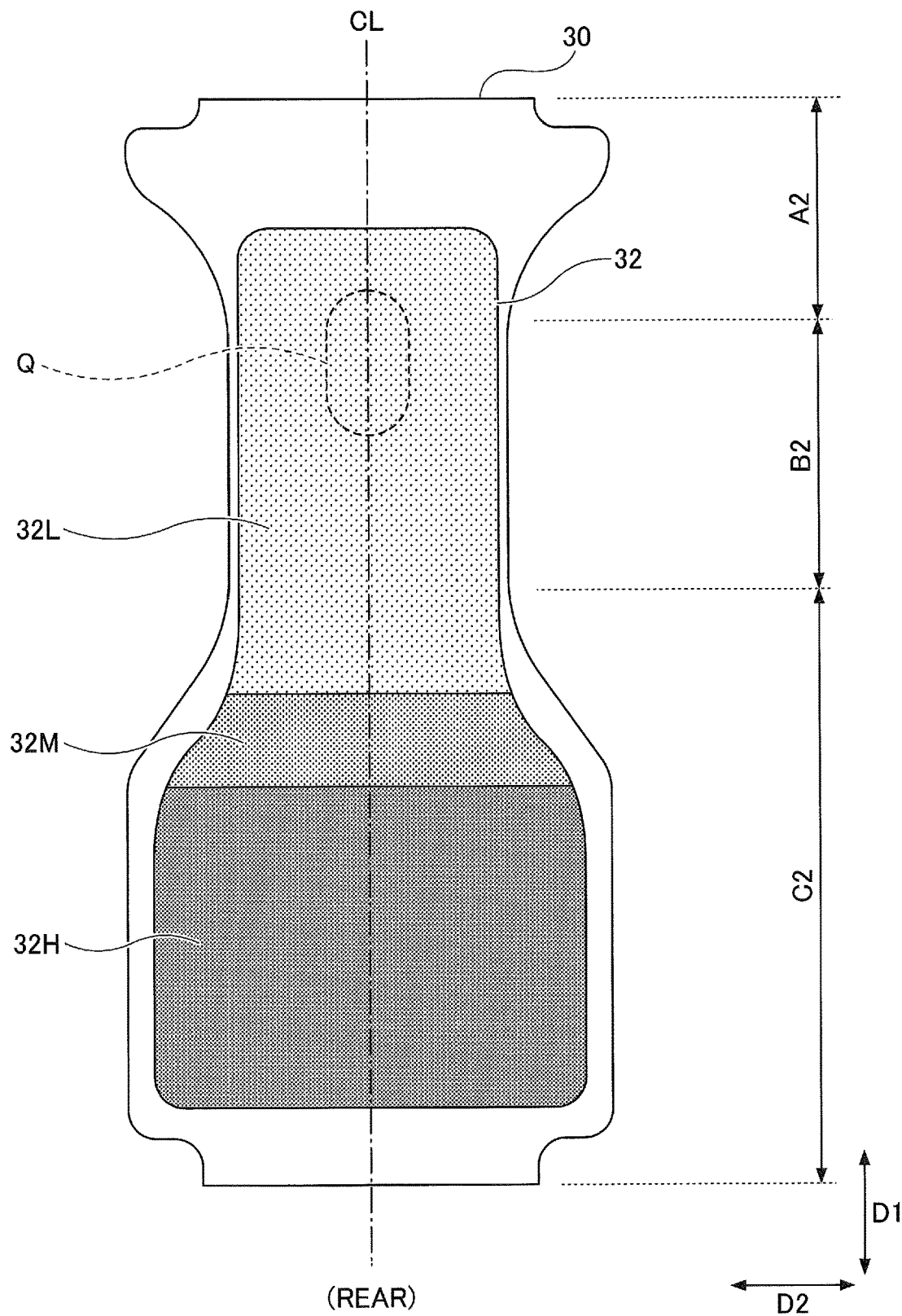
FIG. 3 is a planar view of an absorbent body in the embodiment shown in FIG. 1.

FIG. 3 shows a planar view of the absorbent body 30. As shown in FIG. 3, the absorbent body 30 has an elongated shape as a whole, in the same manner as the absorbent article 100. As illustrated in FIG. 3, the absorbent body 30 may be line-symmetric in shape and configuration with respect to the front-rear direction centerline CL, but the shape and configuration of the absorbent body 30 may not necessarily be line-symmetric. Further, as illustrated in FIG. 3, the absorbent body 30 has a crotch-corresponding region B2 substantially in the middle in the front-rear direction D1, and this crotch-corresponding region B2 corresponds to the above-described crotch-corresponding region B1 of the absorbent article 100. The region adjacent to the front of the crotch-corresponding region B2 and extending to the front edge of the absorbent body 30 is the front region A2, and the region adjacent to the rear of the crotch-corresponding region B2 and extending to the rear edge of the absorbent body 30 is the rear region C2.

In the same manner as the whole shape of the absorbent article 100 in a planar view, the absorbent body 30 may be shaped to have a constricted portion, but may be in a rectangular shape or the like having a constant width and having no constricted portion over the front-rear direction D1, regardless of the shape of the absorbent article 100 in a planar view. When the absorbent body 30 has a constricted portion as in the illustrated embodiment, the minimum width of the constricted portion may be approximately 50 to 75% with respect to the length of the portion forward of or rearward of the constricted portion in the width direction D2.

The crotch-corresponding region B2 of the absorbent body 30, which may form a part of the above-described constricted portion, may be provided in the front half of the absorbent body 30 as illustrated, or may be provided in the middle of the front-rear direction D1 of the absorbent body 30, depending on the overall configuration of the product.

As illustrated in FIG. 3, the absorbent body 30 may have a variable-density portion 32, in which the density varies, at least in the region extending from the crotch-corresponding region B2 to the rear region C2. The variable-density portion 32 is a portion of the absorbent body 30 in which the density increases stepwise or gradually from the front toward the rear. The density of the variable-density portion 32 may be varied based on the fibers or filaments contained in the absorbent body 30 (i.e., a fiber density).

The range over which the variable-density portion 32 extends in the front-rear direction D1 is not particularly limited, as long as the variable-density portion 32 is provided at least in the region extending from the crotch-corresponding region B2 to the rear region C2 as described above. For example, the variable-density portion 32 may not necessarily be in the front region A1, and may extend from any position in the crotch-corresponding region B2 to any position in the rear region C2. The entire absorbent body 30 may be the variable-density portion 32. However, the front edge of the variable-density portion 32 may be positioned forwardly at a distance from the rear edge of the crotch-corresponding region B2, the distance being preferably two-thirds or more, more preferably three-fourths or more with respect to the length of the crotch-corresponding region B2 in the front-rear direction D1. In addition, the front edge of the variable-density portion 32 may preferably be at or beyond the front edge of the crotch-corresponding region B2. The variable-density portion 32 preferably extends in a range that includes the biofluid discharge opening corresponding portion Q, which will be later described.

In the illustrated embodiment, the variable-density portion 32 extends from the rear of the front region A2 to the vicinity of the rear edge of the rear region C2 across the entire crotch-corresponding region B2. The rear edge of the variable-density portion 32 may be positioned at the same position as the rear edge of the absorbent body 30. However, in order to prevent rearward leakage, the rear edge of the variable-density portion 32 may be positioned 10 to 100 mm, preferably 20 to 80 mm forward from the rear edge of the absorbent body 30.

The planar shape of the variable-density portion 32 is not particularly limited, but may substantially be along the contour of the absorbent body 30 in a range over which the variable-density portion 32 extends. For example, as in the embodiment illustrated in FIG. 3, the variable-density portion 32 has a smaller width in the front and a lager width in the rear. According to the embodiment illustrated in FIG. 3, the front edge of the variable-density portion 32 extends in parallel to the width direction D2. However, the front edge may be forwardly convex in the front-rear direction D1, or more forwardly projected as it approaches the front-rear direction centerline CL. The same applies to the rear edge of the variable-density portion 32.

In a state in which the absorbent article is worn in the normal manner, biofluid (such as urine) is drained in the region from the front to the middle of the crotch-corresponding region B2. In other words, the biofluid discharge opening corresponding portion Q corresponding to the biofluid discharge opening such as urethral opening of the wearer when worn, is located substantially from the front to the middle of the crotch-corresponding region B2. In an absorbent article in which the variable-density portion is not provided in the absorbent body, when a large amount of biofluid is discharged at a stretch, the biofluid can only radially spread from the position at which the absorbent body comes into contact with the biofluid, and it is difficult to direct the biofluid in a predetermined direction. Therefore, the biofluid may fail to be absorbed within the crotch corresponding region, and may be leaked laterally. In contrast, according to the present embodiment, the absorbent article 100 has the variable-density portion 32 in which the density is increased from the front toward the rear, so that the biofluid can be directed from the front to the rear by a difference in capillary force in the absorbent body.

In the embodiment illustrated in FIG. 3, the variable-density portion 32 includes a low-density portion 32L, a medium-density portion 32M and a high-density portion 32H disposed from the front to the rear. The low-density portion 32L is a portion having a relatively lower density in the variable-density portion 32, the high-density portion 32H is a portion having a relatively high density in the variable-density portion 32, and the medium-density portion 32M is a portion having a density between the low-density portion 32L and the high-density portion 32H. The densities of the low-density portion 32L, the medium-density portion 32M, and the high-density portion 32H are relative densities. The low-density portion 32L, the medium-density portion 32M, and the high-density portion 32H each may have a uniform density within each portion, or may have a density varying stepwise or gradually within each portion.

In the illustrated embodiment, the variable-density portion 32 is configured to have a rearwardly stepwise increasing density. However, the variable-density portion 32 may be configured to have a rearwardly gradually increasing (continuously increasing) density.

Because the variable-density portion 32 has a stepwise or gradually varying density, the biofluid can be induced rearwardly at an appropriate transfer rate, thereby reducing the area in which the biofluid is transferred at an excessively high rate. This reduces a part of the absorbent body through which biofluid passes without being sufficiently utilized for absorption, and allows for the effective utilization at least of both the crotch-corresponding region B2 and the rear region C2. Thus, the absorbent body 30 can be utilized in a greater extent in the front-rear direction D1.

The density of the low-density portion 32L may be approximately 5 to 20 kg/m$^3$, the density of the medium-density portion 32M may be approximately 10 to 40 kg/m$^3$, and the density of the high-density portion 32H may be approximately 30 to 80 kg/m$^3$. Each of these densities of the low-density portion 32L, the medium-density portion 32M, and the high-density portion 32H may be a uniform density within each portion, or may be varied stepwise or gradually within each portion.

In the specification, the density of the absorbent body can be measured as follows. A part to be measured is cut out from the absorbent body to have a predetermined size, and the area and the weight of the part are measured. Further, the thickness is measured by using a thickness measuring instrument ("Peacock", model number: FFD-7, manufactured by Ozaki Mfg. Co., Ltd.), for example. The density can be calculated from the area, the thickness and the weight measured as above.

The variable-density portion 32 can be formed using any conventional method. For example, fibers may be stacked in a fiber stacking process so as to have a greater basis weight in an area in which a higher density is desired in the absorbent body, and then pressed by press rolls with no protrusion or depression. Alternatively, fibers may be stacked so as to have a homogeneous basis weight as a whole, and then pressed by press rolls that have a protrusion corresponding to an area in which a higher density is desired in the absorbent body. The latter case results in a difference in thickness within the variable-density portion 32. In addition, the variation in density can also be achieved by using different materials to form the low-density portion 32L, medium-density portion 32M, and high-density portion 32H.

Figure 4:
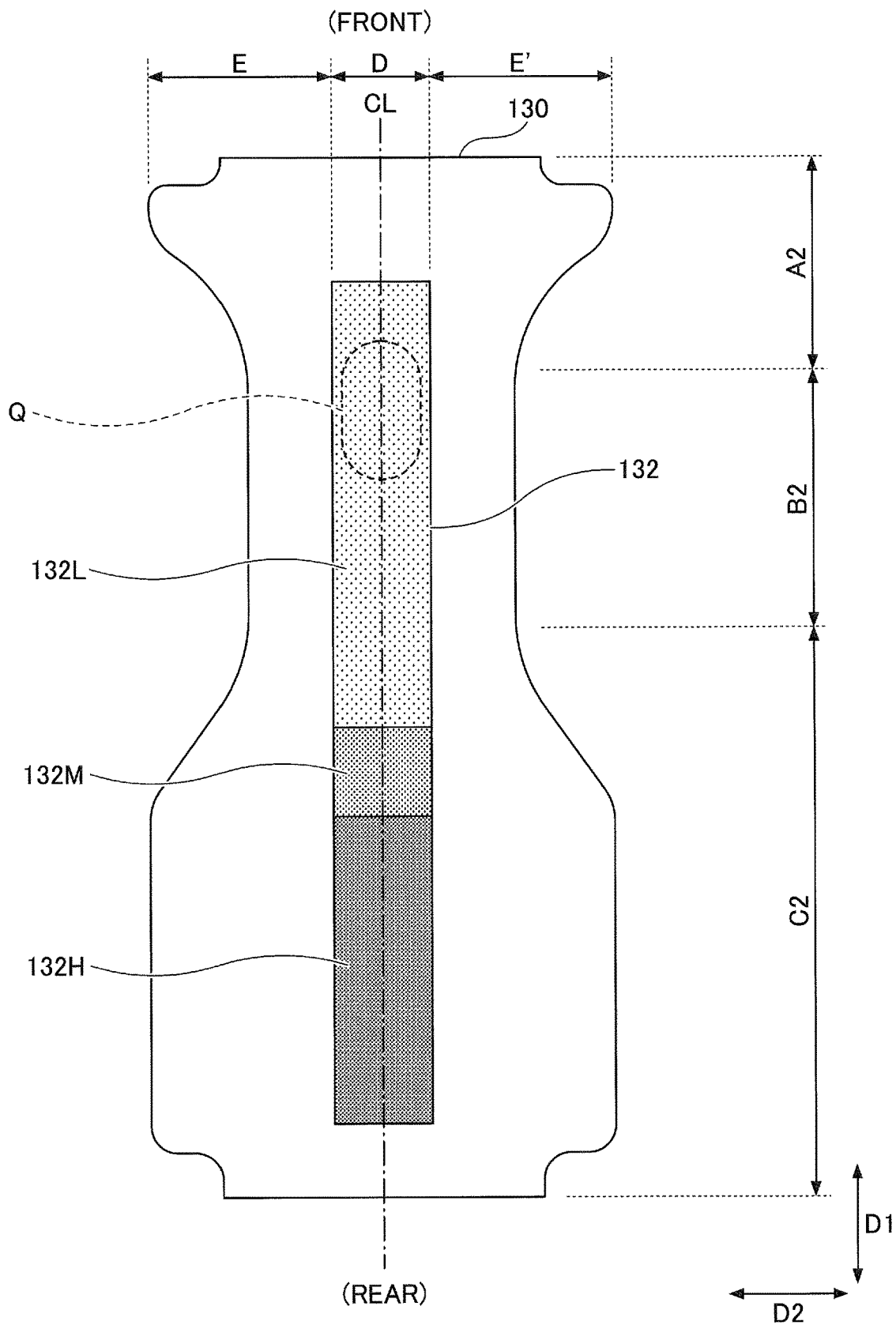
FIG. 4 is a planar view of an absorbent body in another embodiment of the present invention.

FIG. 4 shows a planar view of another absorbent body 130 in the embodiment. In the same manner as the absorbent body 30 illustrated in FIGS. 1-3, the absorbent body 130 also has a variable-density portion 132. The variable-density portion 132 has a low-density portion 132L, a medium-density portion 132M, and a high-density portion 132H from the front toward the rear. The absorbent body 130 differs from the absorbent body 30 (illustrated in FIGS. 1 and 3) in that the size and the shape of the variable-density portion 132 are different. The variable-density portion 132 in the absorbent body 130 has a smaller width than the variable-density portion 32 of the absorbent body 30. Further, the variable-density portion 132 has the same width along the front-rear direction D1.

FIG. 4 illustrates a middle region D including the biofluid discharge opening corresponding portion Q, and lateral regions E and E' each outwardly adjacent to the middle region D in the width direction D2. The variable-density portion 132 is arranged so as to correspond to the middle region D. The variable-density portion 132 may extend over the middle portion D, or may have a width smaller than that of the middle region D and extend within the middle region D. In either case, the variable-density portion 132 is preferably provided at least in the middle region D. This arrangement allows the biofluid to be absorbed immediately at the position where the biofluid is discharged when the absorbent article is worn in the normal manner, and to be effectively dispersed rearwards. The width and the size of the middle region D and the lateral regions E and E' are illustrated only by way of example in the present specification and the drawing, but may depend on the type of absorbent article, the purpose of use (health condition, and sex of the target wearer for the absorbent article), etc. The length of the middle region D may be approximately 10 to 100 mm in the width direction D2.

In the embodiments illustrated in FIGS. 3 and 4, a region other than the variable-density portion 32, 132, which has no density variation (i.e., a region with a substantially uniform density), is provided around the variable-density portion 32, 132. In other words, the density is substantially uniform in a region other than the variable-density portion 32, 132. The density of the absorbent body 30, 130 in a constant density region, is not particularly limited, but preferably has a density lower than the density of the highest density region in the variable-density portion 32, 132. The density of the region without a density variation may also have a density similar to the average density in the variable-density portion 32, 132, or may have a density equivalent to the average density of the density in a location having a highest density and the density in a location having a lowest density in the variable-density portion 32, 132. Alternatively, the region without a density variation may have the same density as the density in any of the low, medium, and high-density portions, or may have the density different from the density in either of the low, medium, and high-density portions. The above density may be an average density in the portion when there is a density difference within the portion.

Further, the thickness of the region without a density variation, which is the region other than the variable-density portion 32, 132, is not particularly limited, and may be larger or smaller than the variable-density portion 32, 132. When there is a thickness difference in the variable-density portion 32, 132, the region without a density variation may have a thickness less than the greatest thickness of the variable-density portion 32, 132, or a thickness greater than the smallest thickness of the variable-density portion 32, 132.

Figure 5:
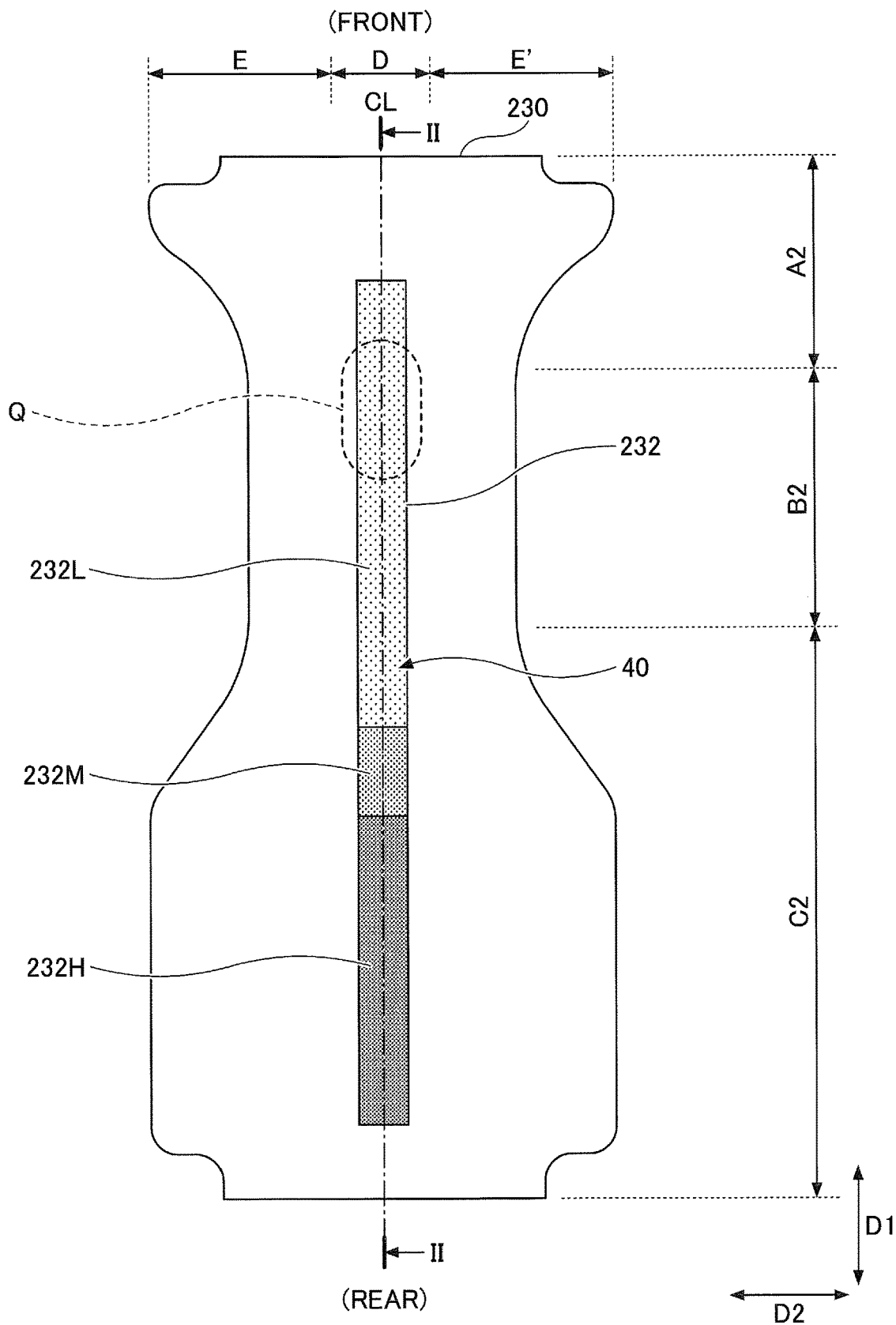
FIG. 5 is a planar view of an absorbent body in yet another embodiment of the present invention.
Figure 6:
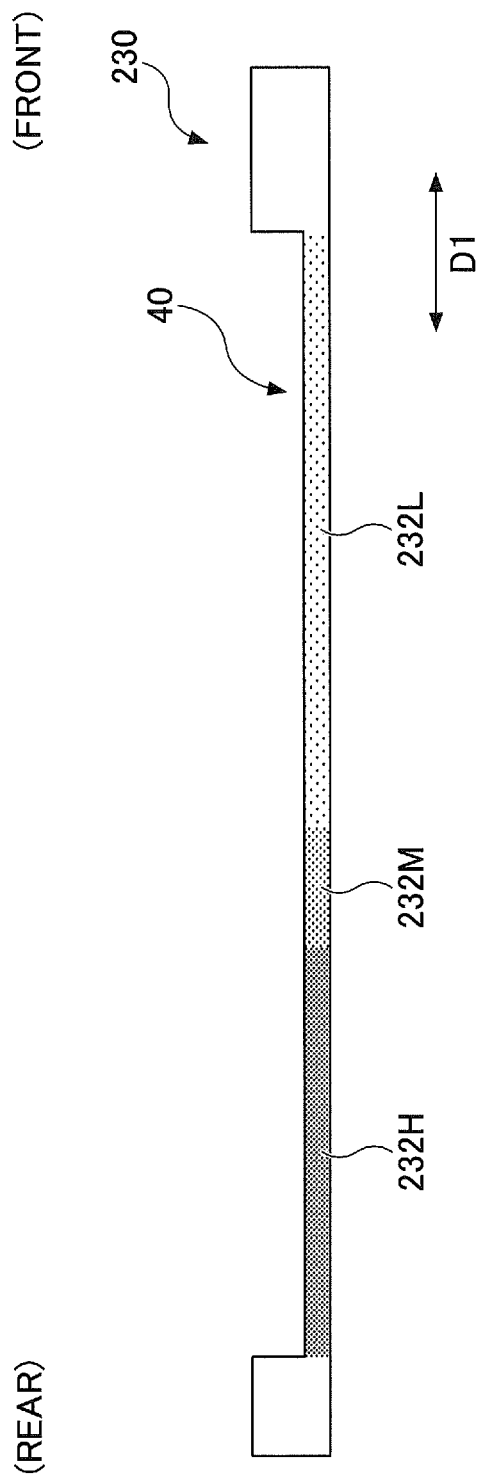
FIG. 6 is a cross-sectional view taken along the line II-II in FIG. 5.

FIG. 5 shows a planar view of the absorbent body 230 in another embodiment. In addition, FIG. 6 shows a cross-sectional view taken along the II-II line in FIG. 5. The absorbent body 230 has a variable-density portion 232, and the variable-density portion 232 has a low-density portion 232L, a medium-density portion 232M, and a high-density portion 232H from the front to the rear, in the same manner as in the absorbent body 30 (FIGS. 1 and 3) and the absorbent body 130 (FIG. 4) described above. However, as illustrated in FIGS. 5 and 6, the absorbent body 230 differs from the absorbent bodies 30 and 130 in that the absorbent body 230 has a groove 40. The groove 40 is a depression toward the backsheet side and lower than the surrounding region. As illustrated in FIGS. 5 and 6, a part of the absorbent body 230 in which the groove 40 is provided, has the variable-density portion 232. More specifically, the part in which the groove 40 is provided, or the part with the groove 40 is the variable-density portion 232. In other words, a low-density portion 232L, a medium-density portion 232M, and a high-density portion 232H are formed within the part in which the groove 40 is provided.

As shown in FIG. 5, the groove 40 extends in the front-rear direction D1 in the absorbent body 230. Specifically, the groove 40 is formed along the front-rear direction centerline CL to straddle the front-rear direction centerline CL in the width direction D2. In the illustrated embodiment, the groove 40 is a single groove extending in the front-rear direction, but may include a plurality of grooves extending in the front-rear direction. In either case, the groove 40 is preferably disposed within the middle region D or near the middle region D. Because the groove 40 may be located within the middle region D as illustrated in FIG. 5, a part of the biofluid can be immediately absorbed at the position where the biofluid is discharged, and unabsorbed biofluid can be directed rapidly rearward.

The width of the groove 40 is preferably 10 to 100 mm, and more preferably 15 to 80 mm. The width of the groove 40 may be constant along the front-rear direction D1 as shown in FIG. 5, but may vary. For example, the width of the groove 40 may be gradually forwardly or rearwardly increased or decreased. The groove may meander, or may be formed in a regular or irregular wavy line.

The groove 40 may extend from the front edge of the absorbent body 330 to the rear edge, but preferably the front edge of the groove 40 is located 10 to 100 mm rearward from the front edge of the absorbent body 330. Further, the rear edge of the groove 40 is located 30 to 150 mm forward of the rear edge of the absorbent body 330. These may ensure a certain absorption capacity of the absorbent body 230 and also maintain the shape of the absorbent body 230.

In the part in which the groove 40 is provided, the thickness of the absorbent body 230 is uniform. However, the thickness is not necessarily constant.

The thickness of the absorbent body 230 within the part with groove 40 is not particularly limited as long as the thickness is less than that of the surrounding area. For example, the thickness of the absorbent body 230 in the part with the groove 40 may be gradually reduced from the front to the rear. In such case, the cross-sectional shape of the groove 40 cut along the front-rear direction D1 may be a long triangle in the front-rear direction D1.

The thickness of the absorbent body in the part with the groove 40 may be 20 to 80%, preferably 30 to 70%, of the thickness of the surrounding area, i.e., the thickness of the absorbent body in the part provided with no groove.

In the embodiment illustrated in FIGS. 5 and 6, a part in which the groove 40 is not provided is a portion having no varied density, or a portion other than the variable-density portion 232. However, the variable-density portion may be formed also in the part in which the groove 40 is not provided in the absorbent body. In that case, the region other than the part with the groove 40 in the absorbent body may have a density stepwise or gradually increasing from the front to the rear. Further, in the absorbent body, the density in the part in which the groove 40 is provided may be substantially the same as the density in the part in which the groove 40 is not provided.

Figure 7:
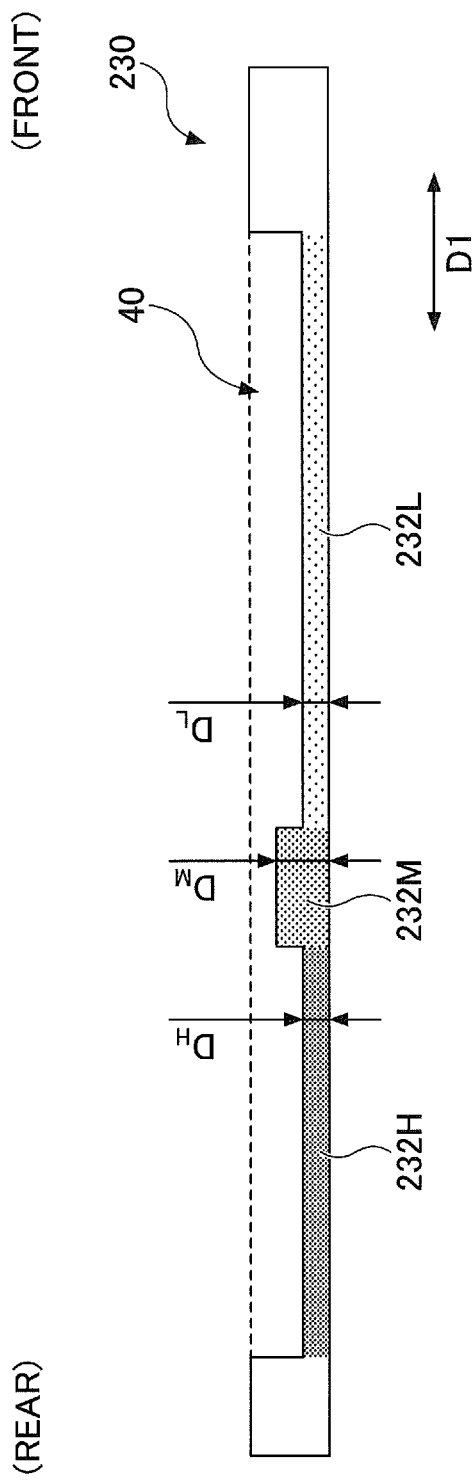
FIG. 7 is a view of a variation of the absorbent body shown in FIGS. 5 and 6.

FIG. 7 shows a variation of the absorbent body 230. The embodiment illustrated in FIG. 7 has the same basic structure as in the embodiment illustrated in FIGS. 5 and 6, but differs in that the former has a raised part in the middle in the front-rear direction D1. In the embodiment illustrated in FIG. 7, the thickness $D_M$ of the medium-density portion 232M is higher than the thickness $D_L$ of the low-density portion 232L located forward of the medium-density portion 232M and the thickness $D_H$ of the high-density portion 232H rearward of the medium-density portion 232M. The greater thickness in the middle of the groove 40 prevents the groove 40 from collapsing even when the absorbent body 230 deforms due to the force from both lateral sides when the absorbent article is worn. In the example illustrated in FIG. 7, the thickness $D_L$ of the low-density portion 232L and the thickness $D_H$ of the high-density portion 232H are the same, but they may be different from each other.

The thickness $D_L$ of the low-density portion 232L may be 20 to 80% and preferably 30 to 70% of the thickness $D_M$ of the medium-density portion 232M. The thickness $D_H$ of the high-density portion may also be 20 to 80%, and preferably 30 to 70% of the thickness $D_M$ of the medium-density portion 232M.

In the embodiment illustrated in FIG. 7, the medium-density portion 232M is preferably located in the rear region C2. In this configuration, the medium-density portion 232M, which is relatively thicker than the thickness in the portion forward thereof and the portion rearward thereof and is protruded from the skin side, is not located in the crotch-corresponding region B2, in which the absorbent article can be more closely attached, but is located in the rear region C2 rearward of the crotch-corresponding region B2. This configuration is preferable in light of reducing uncomfortable feeling when the absorbent article is worn. Alternatively, the medium-density portion 232M can be located within the crotch-corresponding region B2. In this embodiment, a portion having a greater thickness is provided in the crotch-corresponding region B2, in which the groove 40 is particularly likely to collapse. This configuration is preferable in light of preventing the groove 40 from collapsing.

In the embodiment illustrated in FIG. 7, the length of the front-rear direction D1 of the medium-density portion 232M may be 10 to 50 mm, preferably 15 to 40 mm. A length of 10 mm or more enables the groove to be less likely collapse even when a force is applied from the lateral side of the absorbent body 230, thereby maintaining the function of the groove to induce the biofluid rearwardly. A length of 50 mm or less can prevent excessively reducing the soft part in the absorbent body 330, and thus reducing the absorption capacity of the absorbent body 330.

The grooved part illustrated in FIG. 7, in which the thickness $D_M$ of the medium-density portion 232M is greater than the thickness $D_L$ of the low-density portion 232L forward of the medium-density portion 232M and the thickness $D_H$ of the high-density portion 232H rearward of the medium-density portion 232M, can be formed as follows. As illustrated in FIG. 8(a), a stacked fibrous body is prepared to have a smaller basis weight only in an area in which the low-density portion 232L is desired to be formed. Subsequently, the above stacked fibrous body is pressed by using press rolls or a press machine having a shape as illustrated in the upper of FIG. 8(b), i.e., a shape including a less protruded part corresponding to the area in which the medium-density portion 232M is be formed, and a more protruded part corresponding to the area in which the high-density portion 232H is to be formed. This allows the stacked fibrous body to be moderately compressed in the area in which the medium-density portion 232M is to be formed, and to be intensively compressed in the portion in which the high-density portion 232H is to be formed. As a result, an absorbent body 230 having a low-density portion 232L, a medium-density portion 232M, and a high-density portion 232H is formed as illustrated in FIG. 8(b).

Figure 9:
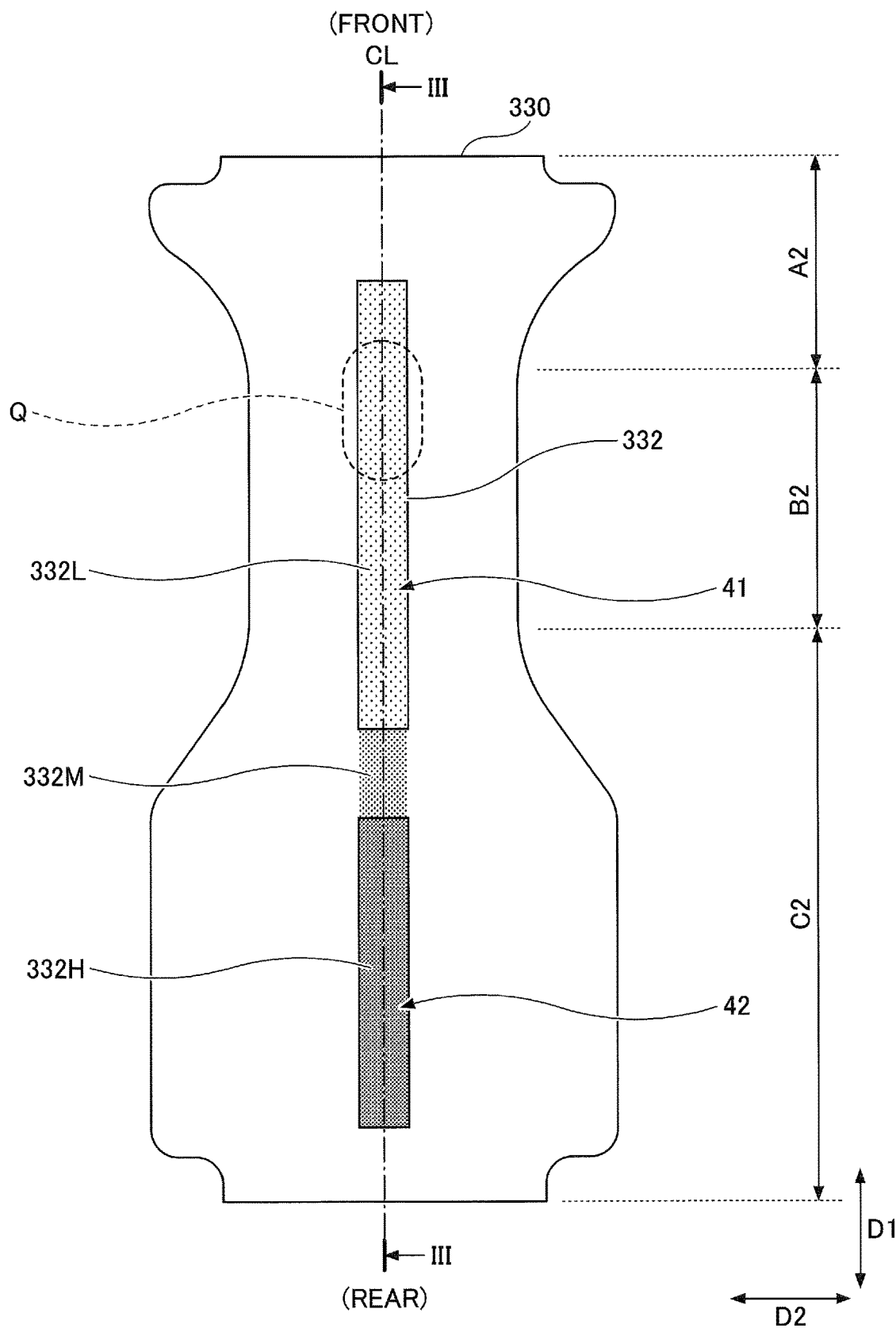
FIG. 9 is a planar view of an absorbent body in yet another embodiment of the present invention.
Figure 10:
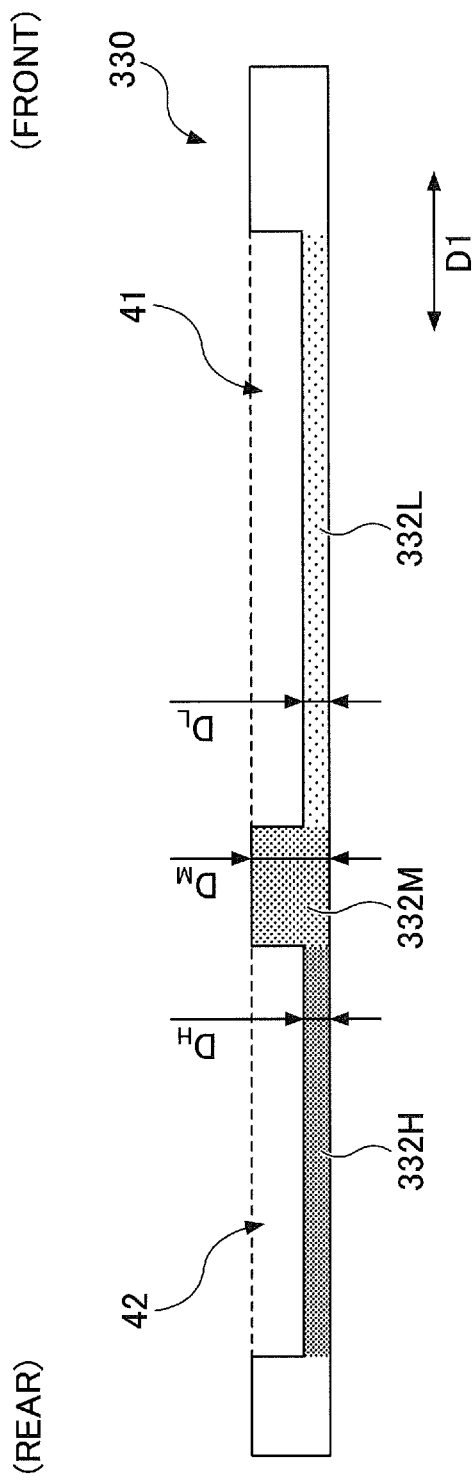
FIG. 10 is a cross-sectional view taken along the line III-III in FIG. 9.

FIG. 9 shows the absorbent body 330 in another embodiment. FIG. 10 shows a cross-sectional view taken along the III-III line in FIG. 9. The absorbent body 330 has a variable-density portion 332, and the variable-density portion 332 has a low-density portion 332L, a medium-density portion 332M, and a high-density portion 332H from the front to the rear, in the same manner as in the absorbent body 230 (FIGS. 5 and 6) described above. In addition, a groove extending from the front to the rear in the front-rear direction is also provided. However, as illustrated in FIGS. 9 and 10, the groove formed in the absorbent body 330 differs from the groove formed in the absorbent body 230 in that the former includes a front groove 41 and a rear groove 42 separately in the front-rear direction.

As illustrated in FIGS. 9 and 10, in the absorbent body 330, a part in which the front groove 41 is provided may include a low-density portion 332L of the variable-density portion 332, and a part in which the rear groove 42 is provided may include a high-density portion 332H of the variable-density portion 332. The part of the absorbent body 230 between the front groove 41 and the rear groove 42 includes a medium-density portion 332M. That is, the absorbent body 330 is configured so that the part between the groove 41 and the groove 42 is the medium-density portion 332M of the variable-density portion 332. Thus, in the absorbent body 330, the distance between the groove 41 and the groove 42 in the front-rear direction D1 can be the length of the medium-density portion 332M in the front-rear direction D1. Further, as illustrated in FIG. 10, the thickness $D_M$ of the medium-density portion 332M may be greater than the thickness $D_L$ of the low-density portion 332L located forward of the medium-density portion 332M and the thickness $D_H$ of the high-density portion 332H located rearward of the medium-density portion 332M.

As described above, the absorbent body 330 has a front groove 41 and a rear groove 42 separately in the front-rear direction D1, so that the biofluid which has been induced along the front groove 41, can be controlled not to be transferred at a stretch to the rear groove 42. Therefore, even when a large amount of fluid is discharged, the momentum of the fluid may be reduced in the medium-density portion 332M provided between the grooves. In addition, when forces are applied from the lateral sides, the groove is less likely collapsed and thus it is possible to maintain the function of the groove to rearwardly induce the biofluid when worn.

The width, the arrangement, the size, and the shape of the groove of the absorbent body 330 may be determined in the same manner as the groove of the absorbent body 230 described with reference to FIGS. 5 to 7. The location of the medium-density portion 332M, and also the configuration of the non-grooved part may be determined in the same manner as the absorbent body 230 described with reference to FIGS. 5 to 7.

Figure 11:
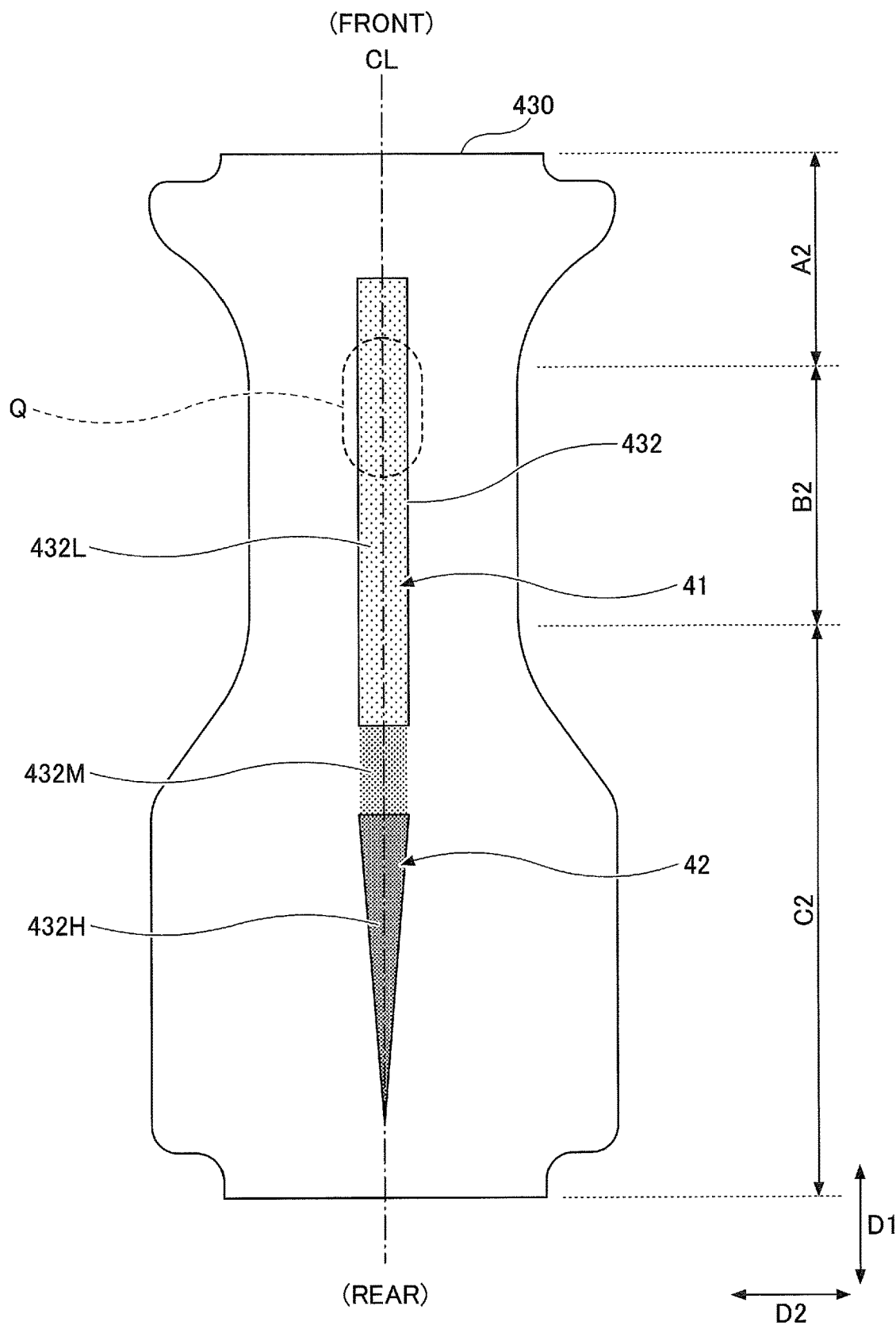
FIG. 11 is a planar view of an absorbent body in yet another embodiment of the present invention.

FIG. 11 shows the absorbent body 430 in another embodiment. The absorbent body 430 has, in the same manner as in the absorbent body 330 illustrated in FIGS. 9 and 10, a variable-density portion 432, which includes a low-density portion 432L, a medium-density portion 432M, and a high-density portion 432H from the front to the rear. The absorbent body 430 also has a front groove 41 and a rear groove 42 separately formed in the front-rear direction. However, the absorbent body 430 differs from the absorbent body 330 (FIGS. 9 and 10) in that the former has the rear groove 42 whose width is rearwardly reduced.

In the absorbent body 430, the wider front end of the rear groove 42 enables biofluid which has been flown behind the front groove 41 to easily enter into the rear groove 42. Further, the biofluid can be more easily diffused from the rear edge of the rear groove 42 into the absorbent body rearward thereof, thereby allowing the rear of the absorbent body to be more effectively utilized.

Besides the width of the rear groove 42, the other configuration of the absorbent body 430 may be determined in the same manner as the groove of the absorbent body 230 described with reference to FIGS. 5 and 7. The location of the medium-density portion 432M and the configuration of the non-grooved part may also be determined in the same manner as in the absorbent body 230 described with reference to FIGS. 5 to 7.

Figure 12:
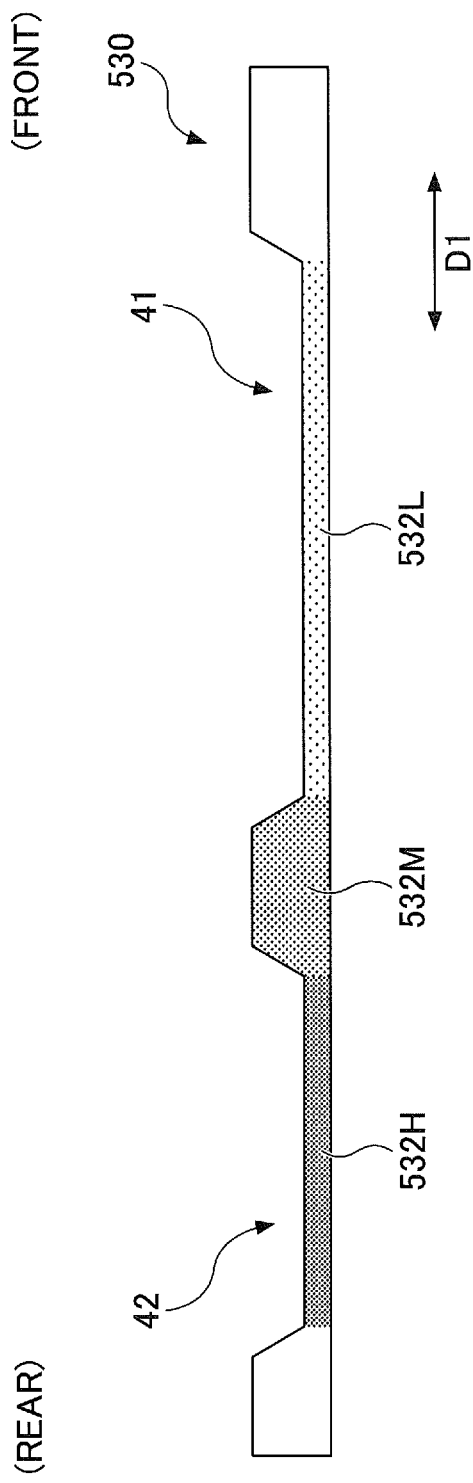
FIG. 12 is a cross-sectional view of an absorbent body in yet another form of the present invention.

FIG. 12 shows a variation of the absorbent body 330 illustrated in FIGS. 9 and 10. The absorbent body 530 illustrated in FIG. 12 has a basic configuration similar to that of the absorbent body 330. Specifically, the absorbent body 530 has a low-density portion 532L, a medium-density portion 532M, and a high-density portion 532H from the front toward the rear. The part in which the front groove 41 is provided includes a low-density portion 532L, the part in which the rear groove 42 is provided includes a high-density portion 532H, and a portion therebetween includes the middle-density portion 532M.

In the absorbent body 530, the front groove 41 and the rear groove 42 have a different cross-sectional shape along the front-rear direction D1 from that in the absorbent body 330 (FIG. 10). Specifically, in the illustrated embodiment, the front groove 41 and the rear groove 42 of the absorbent body 530 are configured to have a shorter length in the front-rear direction D1 in the deeper position of the grooves. In other words, the font groove 41 and rear groove 42 are each shaped in a reverse trapezoid, in which the upper base is longer than the lower base. On the other hand, the medium-density portion 532M is shaped in a trapezoid.

Figure 13:
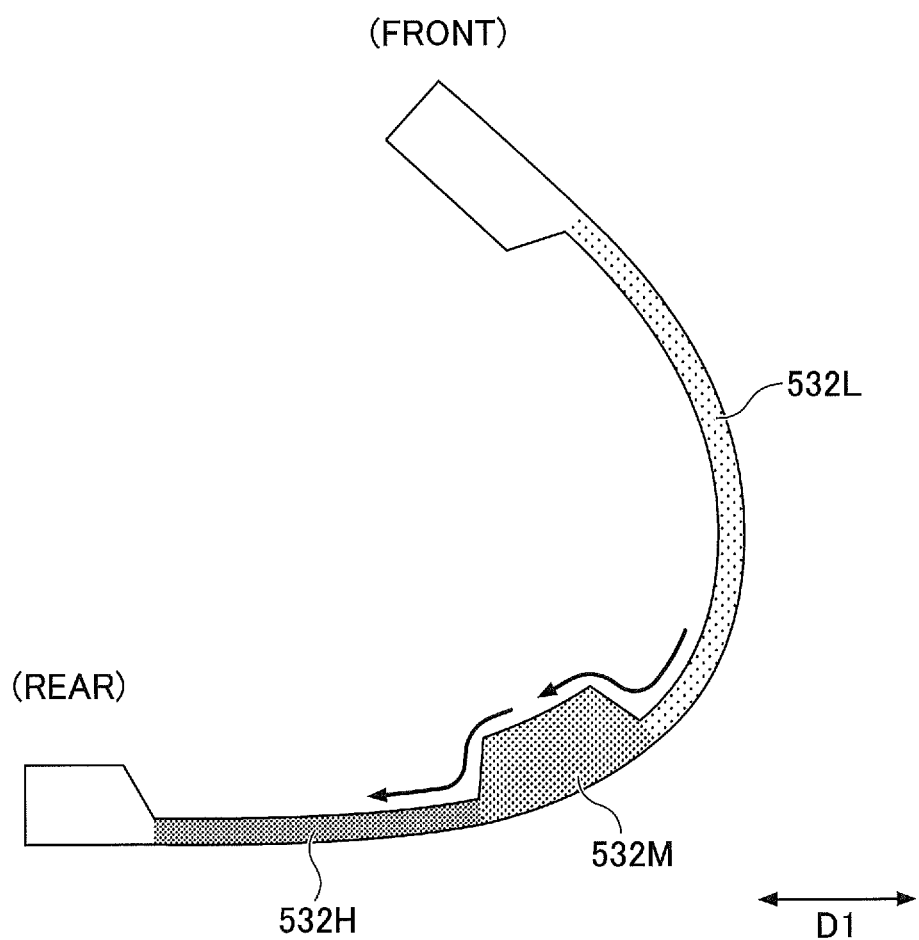
FIG. 13 is a view illustrating the absorbent body shown illustrated in FIG. 12 in a state in which the absorbent article is worn.

FIG. 13 shows a deformed state of the absorbent body 530 when the absorbent article including the absorbent body 530 is worn. In FIG. 13, the direction of the biofluid flow is illustrated with arrows. As described above, the biofluid which has been flown on the surface of the absorbent body 530 to the medium-density portion 532M may be controlled not to excessively rapidly flow toward the rear due to the medium-density portion 532M. In addition to the suppression of a rapid flow, it is also possible to prevent the biofluid from being accumulated in front of the medium-density portion 532M, because the medium-density portion 532M has a trapezoidal cross-sectional shape. This allows fluid to be rearwardly well transferred at an appropriate rate.

Figure 14:
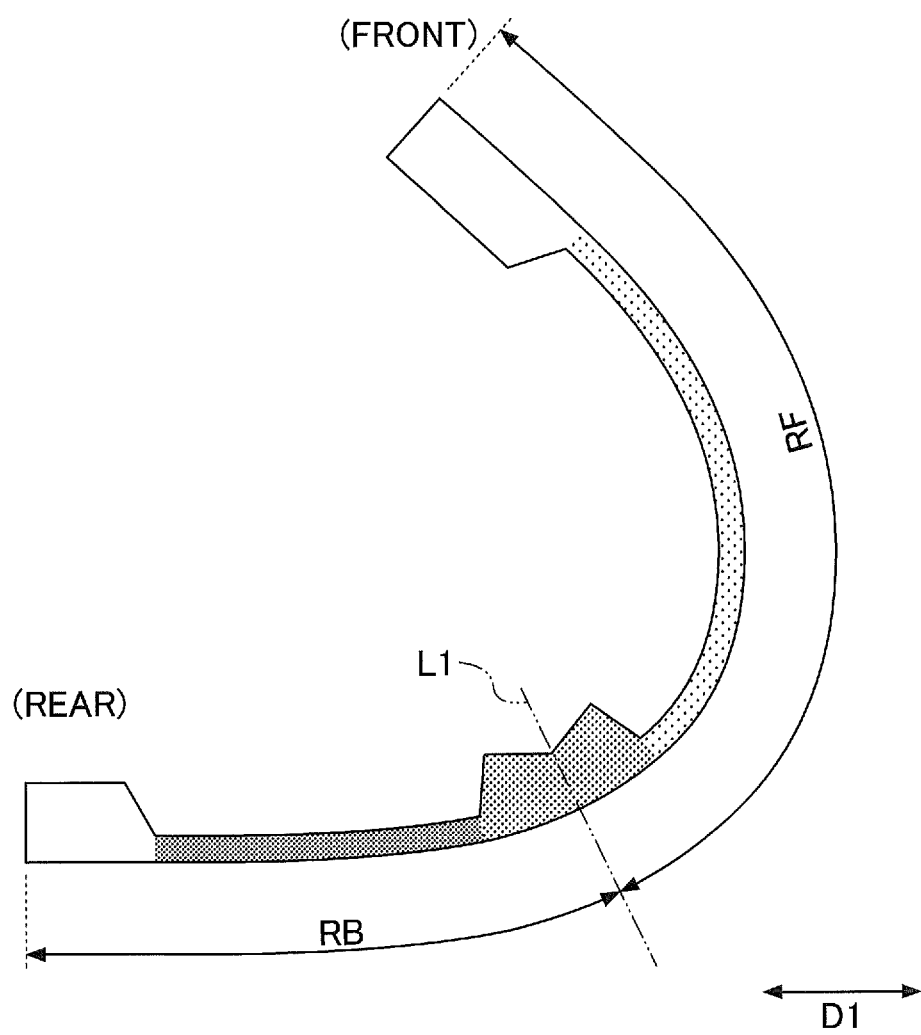
FIG. 14 is a view illustrating a variation of the absorbent body illustrated in FIG. 12 in a state in which the absorbent article is worn.

As illustrated in FIG. 14, the absorbent body 530 may have different configurations between the front part and the rear part of the medium-density portion 532 M of the absorbent body 530, which are bordered by the center of the front-rear direction D1 (represented by line L1). For example, the material or basis weight of the absorbent body 530 may be different between the front part RF forward of the line L1 and the rear part RB rearward of the line L1. With this configuration, when the absorbent article is curved while being worn, the medium-density portion 532 M of the absorbent article 530 easily bends in the middle in the front-rear direction D1, so that the absorbent article is easily deformed.

Although specific embodiments with a pad-type disposable diaper have been described, the present embodiments can be used as a sanitary napkin as well as other forms of disposable diaper, such as a tape-type or an underpants-type diaper. This allows the biofluid, such as urine, menstrual blood, vaginal discharge, and the like, to be rearwardly guided at an appropriate rate.

Hereinafter, preferred embodiments of the present invention will be described.

Appendix 1

An embodiment according to Appendix 1 provides an absorbent article including a liquid-permeable topsheet, a liquid-impermeable backsheet, and an absorbent body provided between the topsheet and the backsheet, wherein the absorbent body includes a crotch-corresponding region corresponding to the wearer's crotch when worn, and a front region being adjacent to and forward of the crotch-corresponding region, and a rear region being adjacent to and rearward of the crotch-corresponding region, and has a variable-density portion with a density increasing stepwise or gradually from a front toward a rear, the variable-density portion being located in a region extending at least from the crotch-corresponding region to the rear region.

In the embodiment according to Appendix 1, a variable-density portion having a density increasing from the front to the rear, and being provided in the region at least extending from the crotch-corresponding region to the rear region, enables the biofluid to be induced from the front to the rear. Accordingly, even when a large amount of biofluid is discharged at a stretch, the absorbent body in the rear region can be sufficiently utilized to prevent biofluid leakage from the lateral sides of the crotch-corresponding region. In this embodiment, the variable-density portion has the density that varies stepwise or gradually, so that the biofluid can be induced rearwardly at an appropriate rate. This allows for the effective utilization of both the crotch-corresponding region and the rear region.

Appendix 2

An embodiment according to Appendix 2 provides that the variable-density portion is located in a middle region, the middle region being located in a middle in a width direction perpendicular to the front-rear direction and including a biofluid discharge opening corresponding portion corresponding to a biofluid discharge opening of a wearer when worn.

In the embodiment according to Appendix 2, the variable-density portion is located in the middle region. With this configuration, the biofluid in a certain amount can be immediately absorbed at the location where the biofluid is discharged in a normal wearing state, and can be successfully rearwardly diffused.

Appendix 3

An embodiment according to Appendix 3 provides that the variable-density portion includes a low-density portion, a medium-density portion, and a high-density portion from the front toward the rear, wherein the absorbent body includes a groove in the front-rear direction, and a part in which the groove is provided includes the variable-density portion.

In the embodiment according to Appendix 3, the groove enables an easy transfer of the biofluid along the groove in the front-rear direction, thereby promoting the above-described diffusion of the biofluid from the front toward the rear. Further, because the variable-density portion includes a low-density portion, a medium-density portion, and a high-density portion from the front to the rear, the biofluid can be diffused rearwardly along the groove at an appropriate rate that is not too fast, and both the crotch-corresponding region and the rear region can be effectively utilized.

Appendix 4

An embodiment according to Appendix 4 provides that the thickness of the medium-density portion is greater than the thickness of the low-density portion and the thickness of the high-density portion.

In the embodiment according to Appendix 4, the thickness of the medium-density portion is greater than the thickness of the high-density portion and the thickness of the low-density portion. Therefore, the groove is less likely collapse, even when a force is applied laterally.

Appendix 5

An embodiment according to Appendix 5 provides that the variable-density portion includes a low-density portion, a medium-density portion, and a high-density portion from the front toward the rear, wherein the absorbent body includes a groove extending in the front-rear direction, the groove including a front groove and a rear groove provided separately in a front-rear direction, and wherein a part in which the front groove is provided includes the low-density portion, and a part in which the rear groove is provided includes the high-density portion, and wherein a part between the part in which the front groove is provided and the part in which the rear groove is provided includes the medium-density portion.

In the embodiment according to Appendix 5, because the front groove and the rear groove are provided, the biofluid can be easily transferred in the front-rear direction along each groove, thereby promoting the above-described diffusion of the biofluid from the front to the rear. Further, because the front groove and the rear groove are separately provided in the front-rear direction, the groove is less likely collapse even when a force is applied laterally. In addition, because the part in which the front groove is provided includes a low-density portion, and the part in which the rear groove is provided includes a high-density portion, and the intermediate part includes a medium-density portion, the biofluid can be transferred rearwardly along the groove at an appropriate rate which is not too fast, and both the crotch-corresponding region and the posterior region can be effectively utilized.

Appendix 6

An embodiment according to Appendix 6 provides that the medium-density portion is provided in the rear region.

In the embodiment according to Appendix 6, the medium-density portion is provided in the rear region, so that the variable-density portion can be disposed in a well-balanced manner in the front-rear direction.

Appendix 7

An embodiment according to Appendix 7 provides that the medium-density portion has a trapezoidal shape in a cross-section cut along the front-rear direction.

In the embodiment according to Appendix 7, in a cross-section along the front-rear direction, the medium-density portion has a trapezoidal shape. With this configuration, the fluid that has traveled on the surface of the absorbent body and reached the medium-density portion may be less likely accumulated in font of the medium-density portion, thereby allowing the biofluid to appropriately rearwardly transfer.

The present application is based on and claims benefit of priority of Japanese Patent Application No. 2018-057861, filed Mar. 26, 2018, the entire contents of which are hereby incorporated by reference.

DESCRIPTION OF THE SYMBOL

21 backsheet
22 topsheet 25 intermediate sheet
30, 130, 230, 330, 430, 530 absorbent body
32, 132, 232, 332, 432, 532 variable-density portion
32L, 132L, 232L, 332L, 432L, 532L low-density portion
32M, 132M, 232M, 332M, 432M, 532M medium-density portion
32H, 132H, 232H, 332H, 432H, 532H high-density portion
80 press mold
100 absorbent article
A1 front region (of absorbent article)
B1 crotch-corresponding region (of absorbent article)
C1 rear region (of absorbent article)
A2 front region (of absorbent body)
B2 crotch-corresponding region (of absorbent body)
C2 rear region (of absorbent body)
D middle region
E, E' lateral region
CL front-rear direction centerline (centerline along first direction D1)
D1 front-rear direction (first direction)
D2 width direction (second direction)
L1 centerline in the width direction of the medium-density portion (centerline along the second direction D2)
RB rearward portion from L1
RF forward portion from L1
Q biofluid discharge opening corresponding region

The invention claimed is:

1. An absorbent article comprising:
a liquid-permeable topsheet;
a liquid-impermeable backsheet; and
an absorbent body provided between the topsheet and the backsheet,
wherein the absorbent body includes
a crotch-corresponding region corresponding to a wearer's crotch when worn,
a front region that is adjacent to and forward of the crotch-corresponding region, and
a rear region being adjacent to and rearward of the crotch-corresponding region, and
has a variable-density portion with a density increasing stepwise or gradually from a front toward a rear, the variable-density portion being provided in a region extending at least from the crotch-corresponding region to the rear region, and
wherein the absorbent body includes a groove extending in a front-rear direction, the variable-density portion being disposed in the groove.

2. The absorbent article according to claim 1,
wherein the variable-density portion is located in a middle region, the middle region being located in a middle in a width direction perpendicular to the front-rear direction and including a biofluid discharge opening corresponding portion corresponding to a biofluid discharge opening of a wearer when worn.

3. The absorbent article according to claim 1, wherein the variable-density portion includes a low-density portion, a medium-density portion, and a high-density portion from the front toward the rear, and
wherein the low-density portion, the medium-density portion, and the high-density portion are disposed in the groove.

4. The absorbent article according to claim 3, wherein the medium-density portion is thicker than the low-density portion and the high-density portion.

5. The absorbent article according to claim 3,
wherein the medium-density portion is provided in the rear region.

6. The absorbent article according to claim 3, wherein the medium-density portion has a top surface and a bottom surface larger than the top surface such that the medium-density portion has a trapezoidal shape in a cross-section cut along the front-rear direction.

7. The absorbent article according to claim 1, wherein the variable-density portion includes a low-density portion, a medium-density portion, and a high-density portion from the front toward the rear,
wherein the groove includes a front groove and a rear groove provided separately in the front-rear direction, and
wherein the low-density portion is disposed in the front groove, and the high-density portion is disposed in the rear groove, and wherein the medium density portion is disposed in a part between the front groove and the rear groove.

8. The absorbent article according to claim 1, wherein the variable-density portion includes a low-density portion, a medium-density portion, and a high-density portion from the front toward the rear, a size of the medium-density portion being smaller than a size of each of the low-density portion and the high-density portion in the front-rear direction.

* * * * *